(12) United States Patent
Lloveras Macià et al.

(10) Patent No.: US 11,464,668 B2
(45) Date of Patent: Oct. 11, 2022

(54) CONTAINER FOR MENSTRUAL COLLECTION AND EMPTYING THEREOF

(71) Applicant: Universität Politécnica de Catalunya, Barcelona (ES)

(72) Inventors: Joaquim Lloveras Macià, Barcelona (ES); Montserrat Iserte Jené, Barcelona (ES)

(73) Assignee: UNIVERSITAT POLITÈCNICA DE CATALUNYA, Barcelona (ES)

( * ) Notice: Subject to any disclaimer, the term of this patent is extended or adjusted under 35 U.S.C. 154(b) by 262 days.

(21) Appl. No.: 16/497,865

(22) PCT Filed: Mar. 28, 2018

(86) PCT No.: PCT/IB2018/052113
§ 371 (c)(1),
(2) Date: Sep. 26, 2019

(87) PCT Pub. No.: WO2018/178887
PCT Pub. Date: Oct. 4, 2018

(65) Prior Publication Data
US 2020/0022835 A1 Jan. 23, 2020

(30) Foreign Application Priority Data
Mar. 28, 2017 (ES) ................ ES201730435

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01)

(58) Field of Classification Search
CPC ....... A61F 5/4553; A61F 5/4404; A61F 5/455
See application file for complete search history.

(56) References Cited

U.S. PATENT DOCUMENTS 1,743,733 A * 1/1930 Emil .................... A61F 5/4553
604/331
2,182,702 A * 12/1939 Previn .................. A61F 5/4553
604/331
(Continued)

FOREIGN PATENT DOCUMENTS

| CN | 205126539 U | 4/2016 | |
|---|---|---|---|
| CN | 106073976 A | 11/2016 | |
| WO | WO-2007082341 A1 * | 7/2007 | ........... A61F 5/4553 |

OTHER PUBLICATIONS

International Search Report and Written Opinion for International Application No. PCT/IB2018/052113, dated Jun. 25, 2018, 11 pages.

*Primary Examiner* — Guy K Townsend
(74) *Attorney, Agent, or Firm* — RatnerPrestia

(57) ABSTRACT

A container for menstrual collection and emptying thereof, in the shape of a cup or of a flat cup, with a drainage tube composed of at least one very flexible thin-walled portion, and a wall portion of greater thickness. By applying an upward force on the portion, the tube is folded by its portion closing off the liquid passageway, and the tube end remaining directly anchored to the vaginal wall or below a hollow formed in the container. For a mid-day emptying, a downward force is applied on the portion to unfold the drainage tube. The horizontal rim of the cup has a number of notches to aid the folding and can have a sloped shape, or double-ringed.

16 Claims, 3 Drawing Sheets

(56) References Cited

U.S. PATENT DOCUMENTS

| | | | | |
|---|---|---|---|---|
| 3,102,541 A * | 9/1963 | Adams | A61F 5/4553 | 604/15 |
| 3,128,767 A * | 4/1964 | Nolan | A61F 6/08 | 604/330 |
| 3,626,942 A * | 12/1971 | Waldron | A61F 6/08 | 604/330 |
| 4,085,755 A * | 4/1978 | Burrage | A61F 5/44 | 604/350 |
| 4,381,771 A * | 5/1983 | Gabbay | A61F 6/08 | 128/836 |
| 4,534,766 A * | 8/1985 | Steer | A61G 7/0503 | 604/350 |
| 4,961,436 A * | 10/1990 | Koch | A61F 6/08 | 128/834 |
| 5,295,984 A * | 3/1994 | Contente | A61F 5/4553 | 604/327 |
| 5,827,248 A * | 10/1998 | Crawford | A61F 5/4553 | 604/328 |
| 6,168,609 B1 * | 1/2001 | Kamen | A61F 5/4553 | 600/573 |
| 6,264,638 B1 * | 7/2001 | Contente | A61M 31/002 | 604/285 |
| 7,875,010 B2 * | 1/2011 | Frazier | A61F 5/455 | 604/347 |
| 8,454,493 B2 * | 6/2013 | La Vean | A61F 6/08 | 600/33 |
| 10,016,308 B2 * | 7/2018 | Knox | A61F 13/00085 | |
| 10,188,545 B2 * | 1/2019 | Conti | A61F 6/12 | |
| 10,357,395 B2 * | 7/2019 | Miller | A61F 5/4404 | |
| 11,219,548 B2 * | 1/2022 | Conti | A61F 6/12 | |
| 11,291,535 B2 * | 4/2022 | Conti | A61F 6/12 | |
| 2002/0143303 A1 * | 10/2002 | Intravartolo | A61F 6/08 | 604/385.18 |
| 2008/0077097 A1 * | 3/2008 | Chambers | A61F 5/4553 | 604/330 |
| 2008/0200888 A1 * | 8/2008 | Gooch | A61F 5/4553 | 604/330 |
| 2010/0312204 A1 * | 12/2010 | Sheu | A61F 5/4408 | 604/330 |
| 2016/0278988 A1 * | 9/2016 | Knox | A61F 15/005 | |
| 2017/0189222 A1 * | 7/2017 | Lin | A61F 5/4553 | |
| 2017/0360594 A1 * | 12/2017 | Park | A61F 5/449 | |
| 2020/0022835 A1 * | 1/2020 | Lloveras Macià | A61F 5/4404 | |

* cited by examiner

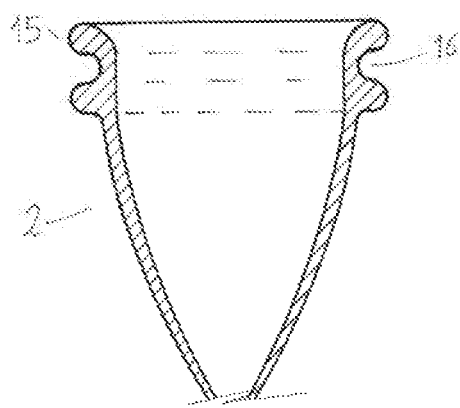 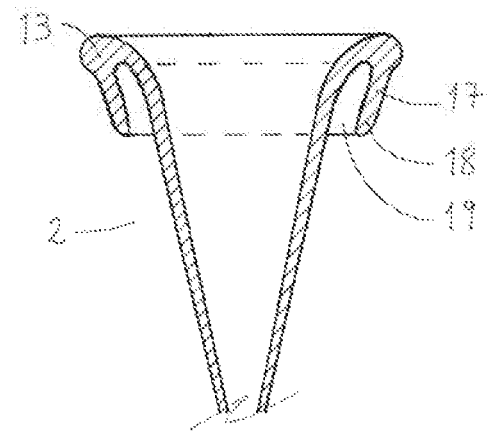
FIGURE 4    FIGURE 5
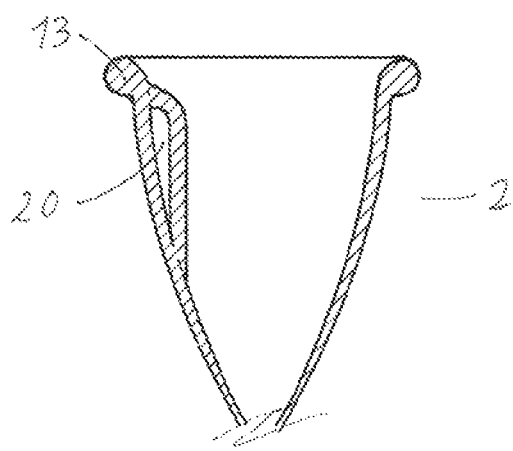
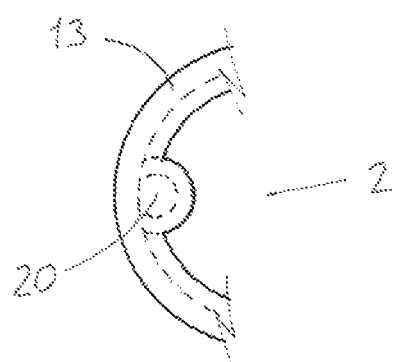
FIGURE 6

CONTAINER FOR MENSTRUAL COLLECTION AND EMPTYING THEREOF

CROSS-REFERENCE TO RELATED APPLICATIONS

This application is the U.S. National Phase Application of PCT/IB2018/052113, filed Mar. 28, 2018, which claims priority to Spanish Patent Application No. P201730435, filed Mar. 28, 2017, the contents of such applications being incorporated by reference herein.

FIELD OF THE ART

The present invention refers to a container intended to be worn by a woman for the collection of the menstrual flow and to the emptying thereof.

STATE OF THE ART

Various types of menstrual vessels, receptacles or containers have been developed over time. Thus, in U.S. Pat. No. 1,743,733, an external menstrual collecting system is designed, and in U.S. Pat. No. 2,182,702 a receptacle collects the liquid directly from the cervix, which is directed to a vessel and which has an external shutoff valve in the tube end for its drainage.

U.S. Pat. No. 5,827,248 is more evolved and similar in some aspects to the present invention. The container has a cup shape and has a drainage tube at its outlet with various valve variants, but none of them like the one shown herein.

DISCLOSURE OF THE INVENTION

The present invention provides a container for the menstrual collection and the emptying thereof, which comprises a cup-shaped body that has a hole in its base that is connected with a flexible tube for the drainage of the menstrual liquid, and a closure system.

The proposed drainage tube has several wall thicknesses; in particular a thin-walled portion and a thick-walled portion, in succession, are proposed, the thick-walled portion having a greater wall thickness than the thin-walled portion, so that the thin-walled portion allows for an easy folding by being weaker, closing itself off by its middle region, blocking the liquid passageway and acting as a valve.

When the proposed menstrual cup is in use, it is inserted in the vaginal cavity, with the cup-shaped body in the deepest part and the drainage tube facing towards the exterior, so that the menstrual flow will be collected by said body and directed towards said duct for its evacuation. The folding of the tube constricts the thin-walled portion collecting the menstrual flow inside the cup-shaped body.

During daily use of the proposed menstrual cup, the tube must be kept folded, and it will be possible to unfold it so in order to empty said menstrual cup without requiring its removal.

According to a first embodiment, the drainage tube has a thin-walled portion adjacent to the container hole and, next, it has the thick-walled portion that has a greater wall thickness than the thin-walled portion.

Alternatively, it is proposed that the drainage tube have a first thick-walled portion adjacent to the hole, next, a second portion corresponding to the thin-walled portion, which is followed by a third thick-walled portion, the second portion having a thinner wall thickness than the first portion and than the third portion. Thereby, it is ensured that the folding of the tube will be produced, first and foremost, by the second thin-walled portion.

The drainage tube may further include a final portion in the end farthest from the container, with a thinner wall thickness than the thick-walled portion, that provides for a gentler contact with the vaginal wall and facilitates its occlusion by pressure.

In order to retain the tube in a folded position during its use, the end of the drainage tube, or at least of the thick-walled portion, may be configured to rest directly on the vaginal wall itself remaining folded. To that end, said thick-walled portion will have a length at least three times its outer diameter.

It is also proposed that the drainage tube end be configured to remain lodged and engaged in a complementary hollow formed in the container, keeping the tube folded.

The cup-shaped container has a perimeter ring in its upper part, or a double perimeter ring having an intermediate gap to improve sealing. Said perimeter ring may include notches that facilitate the folding of the cup for its insertion.

The container body allows for different shapes, such as a cup shape or a flat cup shape, being even liable to be flat.

According to another proposed embodiment, the drainage tube end, when folded, is positioned in a concave area in the side wall of the cup-shaped container that allows completely or partially lodging the tube end, keeping it folded.

Preferably, when the drainage tube is folded, it is lodged in a hollow defined by the inner part of a flange concentric to the cup-shaped container that hangs from the upper rim, and from the outer side wall of the cup.

Alternatively, the drainage tube, when folded, lodges its end in a hollow defined by the inner part of a flange concentric to the cup-shaped container, which hangs from the outer side wall of the cup, below the upper rim, and from the cup's outer side wall itself.

The ring of the upper rim of the container may have between one and four notches that produce a reduction of thickness of said ring in the inner part of the cup in order to ease its folding and insertion. The shape of the upper rim of the ring of the notched container will preferably be sloped relative to the horizontal.

The ring of the container, according to another embodiment, will be a double ring with two rings connected by a gap defined by a membrane or by the cup wall itself.

According to an exemplary embodiment of the proposed menstrual cup, the container in the shape of a flat cup, uncovered underneath, with a greater base diameter measurement than its height, has the upper base in the shape of a disk with a hole from which the drainage tube that has a first portion adjacent to the hole that has a first wall thickness hangs, next the second thin-walled portion that has a thinner wall thickness than the first portion, followed by the third thick-walled portion that has a greater wall thickness than the third thin-walled portion, and ends with a fourth final portion that has a thinner wall thickness than the third thick-walled portion, wherein said upper disk has a rounded rim from which a membrane or a cylinder wall that ends in a ring of similar diameter to that of the upper disk rim hangs, thereby forming a hollow defined by the lower part of the upper disk, the lower ring and the drainage tube, wherein the drainage tube end is lodged when it is folded.

According to another embodiment, the container in the shape of a flat cup, uncovered on top, and having a base diameter measurement greater than its height, has the lower base in the shape of a disk with a hole from which the drainage tube that has a first portion adjacent to the hole that has a first wall thickness hangs, next the second thin-walled portion that has a thinner wall thickness than the first portion, which is followed by the third thick-walled portion that has a greater wall thickness than the third thin-walled portion, and ends with a fourth final portion that has a thinner wall thickness than the third thick-walled portion, wherein said lower base in the shape of a disk has a rounded rim from which a membrane or cylinder wall that ends upwardly in a ring of similar diameter to the lower disk rim protrudes.

BRIEF DESCRIPTION OF THE DRAWINGS

The foregoing and other characteristics and advantages will be more completely understood from the following detailed description of exemplary embodiments that are merely illustrative and non-limiting with reference to the attached drawings, in which:

FIG. 4 shows a section of the cup (2) with a double ring (15) in its upper rim, with a gap between rings (16);

FIG. 5 is a section of a cup (2) cut underneath, with a concentric skirt or flange (17) joined to the upper rim (13) of the cup, this flange having a lower rim (18) that defines a hollow (19) between the flange and the outer wall of the cup (2). The drainage tube end (3) may be inserted in this hollow (19) when it is folded. The shape of the side walls of said cup (2) is a straight cone;

FIG. 6 portrays in its upper part a section of a cup (2) that has a concave area (20) in the side wall to completely or partially lodge the drainage tube end (3) when it is folded upwards. The lower part of the figure corresponds to a plan view of a part of the interior of the cup (2) showing the upper rim (13) and the side wall of the cup (2) deformed inwardly by the concave area (20);

DETAILED DISCLOSURE OF EMBODIMENTS

Figure 1:
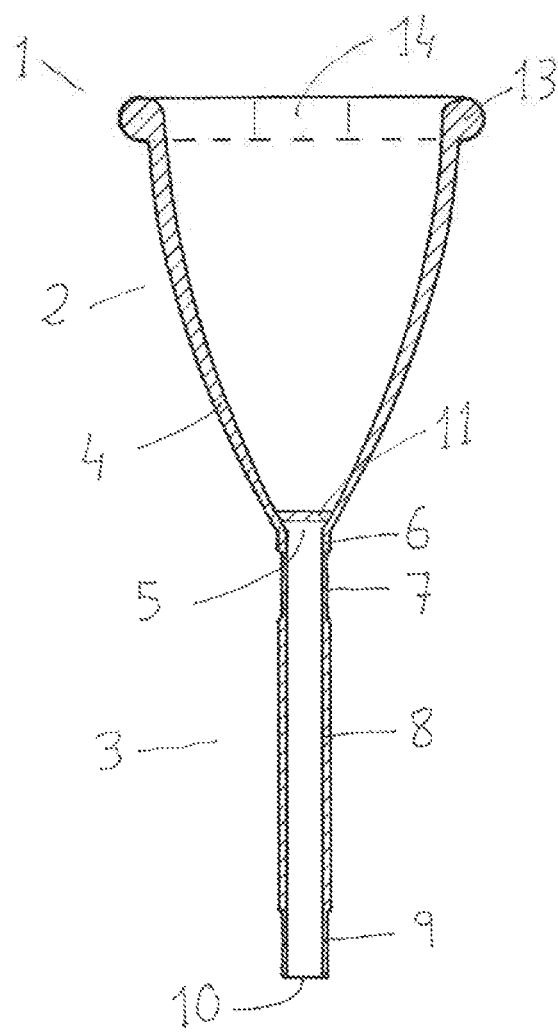
FIG. 1 is an elevational sectional view of a container for the menstrual collection and emptying thereof according to a first embodiment of the present invention.

Without their having a limiting character, several exemplary embodiments of the present invention are discussed next relating to a container 1 for the menstrual collection and the emptying thereof.

In the attached figures, basically two types of containers 1 are shown, one in the shape of a cup 2 and another in the shape of a low cylinder, or thick disk, or flat cup 21. They have a drainage system through a tube 3 that can be actuated at will, it being especially indicated for a mid-day emptying without having to remove the whole container.

The flat cup 21 shape is the minimum expression of a container with a drainage tube 3 to collect menstruation flow.

Possible combinations may also exist among the aforementioned shapes. The advantages of some of these inventions may be summarised in an ease of insertion, reliability of operation, mid-day emptying without the need to remove the whole container, shape and material simplicity and, therefore, their being inexpensive.

The novel embodiments that are presented are improvements to existing devices and basically consist in the drainage tube 3, that has parts of various wall thicknesses 6, 7, 8, 9 but, preferably, with the same inner diameter; that is, a constant inner diameter, whereby the greater outer diameters protrude towards the exterior. The constant inner diameter favours the flow of vaginal flow and facilitates cleaning.

The essence of the operation of the drainage tube 3 as a valve lies in in the second thin-walled portion 7 and in the third normal wall portion 8, allowing the easy folding of the second portion 7, by its being weaker than the adjoining portions 6 and 8, which, this way, is closed off by its middle region 12, blocking the liquid passageway therethrough, acting thereby as a valve.

It will be understood that the so-called normal wall and the so-called thin wall refer to comparative thicknesses; that is, the thin wall is a wall of smaller thickness than the so-called normal wall, and the normal wall has greater thickness than the so-called thin wall, without thereby establishing any thickness interval.

A first portion 6 of the drainage tube 3 may optionally exist joined to the outlet of the hole 5 and having a thickness normal or greater than normal, the second portion 7, having a wall thickness of the thin tube smaller than the first portion 6, remaining between the first portion 6 and the third portion 8. In case the first portion 6 does not exist, the second portion 7 beings directly from the cup base 2.

The occlusion by folding the second portion 7 is produced when portions of said second portion 7 form, relative to each other, an angle lower than approximately 80°. To carry out the folding of the second portion 7 the third portion 8 of the tube 3 is pushed towards the container 1. Since the third portion 8 has normal thickness and is, therefore, less flexible than the second thin portion 7, the folding will be produced, first and foremost, by said second portion 7.

To maintain the tube folded upwards, the end part of the third portion 8 may rest directly on the vaginal wall, which makes it remain in this position, since the third thicker wall portion 8 of the tube 3 would need a force to move it from this position greater than that which is exerted by the second thinner wall portion 7. To unfold the tube 3, the user must overcome this force stretching said third portion 8 downwardly, positioning the whole tube 3 in a straight or extended position, especially positioning the parts of the second portion 7 forming an angle to each other of approximately 180°, and thus carrying out the drainage operation. To place the tube 3 once again in the usage position of the container 1, the reverse operation is carried out, pushing the third portion 8 upwards, whereby the tube is folded by its second thin-walled portion 7, closing off the liquid passageway.

Alternatively, retention systems of the drainage tube 3 in the folded position are presented, those retention systems being integral with the container itself 1, such as: the insertion of the tube end 3 below a concentric skirt or a flange 17 of the cup 2, and which can be hung directly from the upper rim 13 of the container 1, or else said flange protruding midway up the side wall of the cup 2, in an area underneath the upper rim 13. A similar case is the insertion of the drainage tube end 3 in the hollow defined by the disk 22, the membrane 24 and the lower ring 25. Another retention solution of said tube end 3 relative to the cup 2 is also presented, with a concave area 20 that is an inwards distortion of the side wall of the cup 2, in which the surface exterior to the cup is cylindrical, where it allows to completely or partially lodge the drainage tube end 3 when it is in the folded position. Said concave area 20 has an open cylindrical shape and, depending on its depth, it may partially or completely lodge the drainage tube end 3 to which it is attached. In case it lodges it completely, the tube end is snap-fitted through a slot that said cylindrical surface may have.

So, the retention of the folded drainage tube 3 may occur in any position if it rests directly on the vaginal wall or is inside the hollow 19 that defines a flange concentric to the cup, or in the hollow 26 of a container 1 in the shape of a cylinder of greater base diameter than its height, which evokes the shape of a large tablet. Otherwise, the solution of the concave area 20 in the cup wall 2, which is discretional, i.e., may only be placed in a concave area, or several, but not in any position. Similarly, discretional holes could be made below the flanges or else in a partial flange 17, both in the cup 2 and in the flat cup 21.

The tube 3 may optionally have at its disposal a fourth thin-walled portion 9 arranged following the third portion 8. In such a case, the retention of the folded tube 3 will be carried out primarily through said fourth portion 9.

The outlet hole 10 of the tube 3 will be in its end, which will remain positioned in the third portion 8 or, in the case of the existence of a fourth portion 9, in said fourth portion 9.

A mesh 11 over the outlet hole 5 acts as a filter of potential lumps so that the drainage tube 3 will not be clogged.

The vacuum effect that users may experience when extracting the cup is usually broken by the entrance of air through small holes drilled in the side wall of the cup, just below the ring corresponding to the upper rim of the cup. These small holes are sloped relative to the surfaces of the side wall of the cup and usually have a diameter between 1 and 2 mm. In the case of the invention, they might still exist, but they make no sense if the cup 2 is inserted with the drainage tube 3 open extended without folding, whereby it connects the atmospheric pressure with the air inside. Likewise, during the extraction, if the folding is removed and the drainage tube 3 is extended emptying its contents and the user later goes on to the complete extraction of the container 1 with said tube 3 open, there will be no vacuum effect.

Said invention does not seem to exist for these devices, and neither do the retention systems of the upwardly folded tube to keep the liquid passageway closed off. Said system makes the container 1 with drainage and a valve system have a very simple design, and simple materials and manufacturing.

One or several notches 14 in the inner part of the ring of the upper rim 13 of the cup 2, makes the wall thickness smaller in these notches, which causes its weakening, and any folding stress will be smaller, in addition to being less bulky and more compact. Four notches 14, diametrically opposed and equidistant to each other, makes it possible, for one of the most usual foldings of the cup, to apply less force than in the same cup without notches, and that said folding results in a smaller volume and, therefore, makes its insertion easier.

The purpose of a double ring 15 of the upper part of the cup is to improve sealing against possible drop leakage. This double seal 15 has a separation gap 16 between the rings. Sealing is more certain this way.

A container 1 in the shape of a flat cup 21 or low cylinder is hollow underneath. Its upper base is a disk 22 with a hole 5 from which the drainage tube 3 hangs, which, when it is in a folded position by its thinnest wall area 7, acts as a valve closing the passageway for the bleeding that temporarily gathers in the vaginal cavity itself, until it is emptied by means of the drainage tube 3.

The drainage tube 3, when folded, allows to anchor its end 9 and/or 8 in the hollow 26 formed below the disk 22, the membrane walls 24 and the lower ring 25. The mid-day emptying, without the removal of said flat cup, is achieved by applying a downwardly small force on the third portion 8 of the tube, whereby the end 9 and/or 8 will come out of the hollow 26 to extend the tube and thereby empty the container. To resume its use, the reverse operation is carried out, applying an upward force on the third portion 8 so that it folds by its second thinner wall portion 7 and overcoming the resistance, so that the end 9 and/or 8 enters once again the hollow 26 below the disk 22.

Similarly, the container 1 in the shape of a flat cup 21 or low cylinder, may have the disk 22 positioned at mid-height of the cylinder or at the bottom. In the low position, the disk 22 would be the lower base of the cylinder and it would be uncovered on top. The hole 5 of the disk 22 from which the drainage tube 3 hangs, has a first normal wall thickness portion 6, a second thin-walled portion 7, a third normal wall thickness portion 8 and a fourth thin-walled portion 9; in addition, said lower disk has a rounded rim from which a membrane 24 or cylinder wall protrudes that ends on top in a ring of similar diameter to that of the lower disk rim, a hollow being thus formed on top that completely or partially collects the menstrual liquid, when the drainage tube 3 is folded and does not allow the liquid to pass. In this case, the drainage tube end 3 rests directly on the vaginal wall. The menstrual flow may be emptied through the drainage tube 3 when it is stretched from its position by its third portion 8 and said tube is extended.

Figure 2:
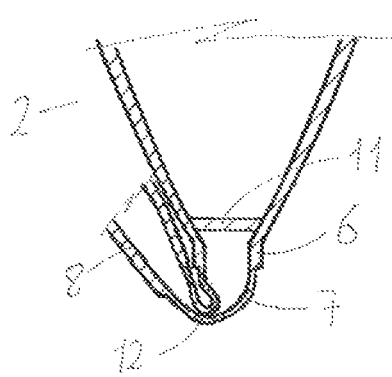
FIG. 2 is a sectional view of the bottom of a cup (2) and of the beginning of the drainage tube (3) of the container of FIG. 1 when the drainage tube is folded upwards by its second portion (7), which is the weak part as a result of having a thin wall, the closing-off area (12) being followed by the third portion (8) of the drainage tube (3)
Figure 3:
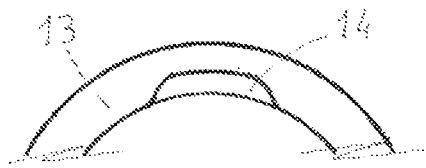
FIG. 3 portrays the upper rim (13) of cup (14) having one notch.
Figure 7:
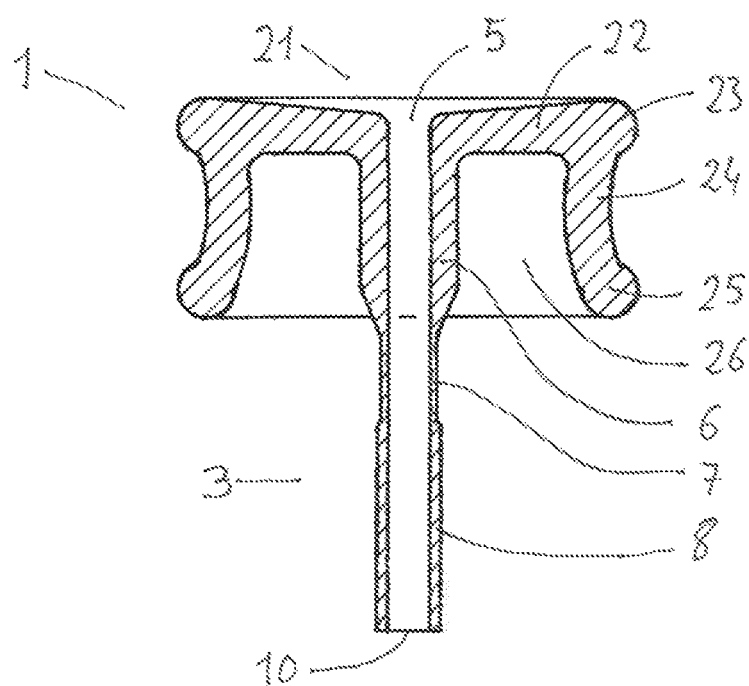
FIG. 7 is an elevational sectional view of a container (1) that is a revolution body symmetrical relative to its centre axis and has a low cylindrical shape (21) that evokes a thick disk or a large round tablet, hollow underneath, from which the drainage tube (3) hangs. It has an upper disk (22) somewhat sloped towards the hole (5), from whose rims the drainage tube (3) protrudes with its different parts of different thicknesses (6), (7), (8) and (9). From the rim of the upper disk (23) a membrane (24) hangs whose lower end is a ring (25). This defines a hollow (26) among the disk, membrane, ring and drainage tube, which will be where the drainage tube end (3) will be lodged when it is folded.

Reference is firstly made to a first embodiment shown in FIGS. 1 to 3, in which the container 1 has the shape of a cup 2 with a drainage tube 3 in its lower part. In the cross-section, the wall thicknesses 4 of the cup 2 are shown, as well as those of the drainage tube 3. The hole 5 connects the bottom of the cup 2 with the drainage tube 3 that has its outlet 10. A mesh 11 integral with the bottom of the cup acts, in use, as a lump filter.

The first portion 6 of the drainage tube 3 has a normal wall thickness as compared with the second portion 7 that has a thin wall thickness. It is followed by the third normal thickness portion 8 and a fourth thin-walled end portion 9.

The container 1 has the shape of a cup 2 from which base a drainage tube 3 protrudes connected with the interior of the cup 2 through a hole 5 and with the exterior through the outlet hole 10.

The upper rim 13 of the cup 2 is like a ring with an approximately circular section and has a notch labelled as 14.

The drainage tube 3 does not have a first portion, or it is negligible, but rather directly has the second thin-walled portion 7 that is attached to the lower end of the cup. Said portion 7 has a thin wall thickness that adds a lot of flexibility to that area. It is followed by a central part or third portion 8 of tube wall thickness greater than the former, which ends in the fourth portion 9 with a thin wall thickness similar to that of the second portion 7.

In use, the tube 3 is folded by weak part 7 by pushing it upwardly by the central part 8, the tube being closed off in this area 12. This way, the passageway for the liquid is closed and the end 9 is placed below the upper rim 13 of the cup, between the side wall of the cup and the vaginal wall, which remains anchored in this position.

If necessary, one or more strips over the hole act as a mesh 11, to filter the liquid and retain the lumps.

The shape of the side walls of the cup 2 is rather conical or parabolic and quite slender, topped in its upper rim 13 by a ring with a solid interior of the same material as the cup and having some thickness.

The upper rim 13 of the cup 2 has four diametrically opposed notches 14 in pairs and equidistant to each other that will act to improve the folding for the insertion of said cup 2.

It will be understood that the different parts that make up the invention described in an embodiment may be freely combined with the parts described in other different embodiments, even if said combination has not been explicitly described, provided the combination is not detrimental.

The invention claimed is:

1. A container for menstrual collection and emptying thereof, said container comprising a cup-shaped body, a flexible drainage tube connected to a hole in a base of the cup-shaped body for the drainage of menstrual liquid, and a closure system,
   wherein the drainage tube having a thin-walled portion and a thick-walled portion succeeding one another, the thick-walled portion having a greater wall thickness than the thin-walled portion, so that the thin-walled portion allows for an easy folding by being weaker, closing itself off by its middle region, blocking the liquid passageway and acting as a valve constituting the closures system, wherein the drainage tube has a constant inner diameter, whereby the thick-walled portion has a greater outer diameter than the thin-walled portion and the greater outer diameter protrudes towards the exterior of the drainage tube, and
   wherein:
   the container further comprises a complementary hollow formed therein, and the drainage tube has an end configured to be lodged in the complementary hollow when the drainage tube is folded by the thin-walled portion; or
   a concave area is formed in a side wall of the cup-shaped body and the drainage tube has an end that, when the drainage tube is folded by the thin-walled portion, is positioned in the concave area, the concave area allowing fully or partially lodging the end of the drainage tube.

2. The container according to claim 1 wherein the drainage tube has a thin-walled portion adjacent to the hole of the container and, next to it, it has the thick-walled portion that has a greater wall thickness than the thin-walled portion.

3. The container according to claim 1 wherein the drainage tube has a first thick-walled portion adjacent to the hole, next a second thin-walled portion, which is followed by a third thick-walled portion, the second thin-walled portion having a wall thickness thinner than the first thick-walled portion and than the third thick-walled portion.

4. The container according to claim 1 wherein the drainage tube further includes a final portion at the distal end of the drainage tube and said final portion has a thinner wall thickness than the thick-walled portion.

5. The container according to claim 1 wherein the drainage tube has an end configured to rest directly on the vaginal wall itself when the container is in use and the drainage tube is folded by the thin-walled portion.

6. The container according to claim 1 wherein the cup-shaped body has a perimeter ring in an upper rim thereof.

7. The container according to claim 6 wherein the ring is a double perimeter ring.

8. The container according to claim 6 wherein the perimeter ring has notches in an inner part thereof.

9. The container according to claim 1 wherein the cup-shaped body has the shape of a flat cup.

10. The container according to claim 1 wherein the cup-shaped body has an outer side wall and a flange concentric thereto hanging from an upper rim of the cup-shaped body at an outer side of the outer side wall, a hollow being defined between the flange and the outer side wall, and wherein the drainage tube, when folded, is lodged in the hollow.

11. The container according to claim 1 wherein the cup-shaped body has an outer side wall and a flange concentric thereto hanging from the outer side wall of the cup-shaped body below an upper rim thereof at an outer side of the outer side wall, a hollow being defined between the flange and the outer side wall, and wherein the drainage tube, when folded, is lodged in the hollow.

12. The container according to claim 8 wherein the perimeter ring of the upper rim has between one and four notches that produce a reduction of thickness of said ring in an inner part of the cup-shaped body in order to ease the insertion.

13. The container according to claim 10 wherein the notched perimeter ring has an upper rim the shape of which is sloped relative to the horizontal.

14. The container according to claim 7 wherein the double perimeter ring has two rings and a gap between the two rings.

15. The container according to claim 9 wherein the flat cup is uncovered underneath, has a base diameter measurement greater than its height, has an upper base in the shape of a disk having the hole from which the drainage tube hangs, the drainage tube has a first thick-walled portion adjacent to the hole that has a first wall thickness, next a second thin-walled portion that has a thinner wall thickness than the first thick-walled portion, followed by a third thick-walled portion that has a greater wall thickness than the second thin-walled portion, and ends with a fourth final portion that has a thinner wall thickness than the third thick-walled portion, and wherein said upper disk has a rounded rim from which a membrane or a cylinder wall that ends in a ring of similar diameter to that of the rounded rim hangs, a hollow being defined by a lower part of the upper disk, the lower ring and the drainage tube, the drainage tube having an end which is lodged in the hollow when the drainage tube is folded.

16. The container according to claim 9 wherein the flat cup is uncovered on top, has a base diameter measurement greater than its height, has a lower base in the shape of a disk having the hole from which the drainage tube hangs, the drainage tube has a first thick-walled portion adjacent to the hole that has a first wall thickness, next a second thin-walled portion that has a thinner wall thickness than the first thick-walled portion, which is followed by a third thick-walled portion that has a greater wall thickness than the second thin-walled portion, and ends with a fourth final portion that has a thinner wall thickness than the third thick-walled portion, wherein said lower base in the shape of a disk has a rounded rim from which a membrane or a cylinder wall that ends upwardly in a ring of similar diameter to a lower disk rim protrudes.

* * * * *